US009610395B2

(12) United States Patent
Maierhofer et al.

(10) Patent No.: US 9,610,395 B2
(45) Date of Patent: *Apr. 4, 2017

(54) DEVICE FOR REVERSING THE BLOOD FLOW FOR AN EXTRACORPOREAL BLOOD TREATMENT DEVICE AND METHOD FOR DETERMINING THE REVERSAL OF THE BLOOD FLOW DURING AN EXTRACORPOREAL BLOOD TREATMENT

(71) Applicant: Fresenius Medical Care Deutschland GmbH, Bad Homburg (DE)

(72) Inventors: Andreas Maierhofer, Schweinfurt (DE); Malte Gross, Ulm (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 162 days.

This patent is subject to a terminal disclaimer.

(21) Appl. No.: 14/306,570

(22) Filed: Jun. 17, 2014

(65) Prior Publication Data

US 2014/0291565 A1  Oct. 2, 2014

Related U.S. Application Data

(63) Continuation of application No. 13/123,290, filed as application No. PCT/EP2009/007066 on Oct. 2, 2009, now Pat. No. 8,784,353.

(30) Foreign Application Priority Data

Oct. 8, 2008  (DE) .................. 10 2008 050 849

(51) Int. Cl.
*A61M 1/36* (2006.01)
*F16K 11/074* (2006.01)
(Continued)

(52) U.S. Cl.
CPC ............ *A61M 1/367* (2013.01); *A61M 39/10* (2013.01); *A61M 39/105* (2013.01);
(Continued)

(58) Field of Classification Search
CPC .... A61M 1/3656; A61M 1/367; A61M 39/10; A61M 39/105; A61M 39/223;
(Continued)

(56) References Cited

U.S. PATENT DOCUMENTS 7,503,902 B2 * 3/2009 Jensen ................ A61M 39/223
251/149.2
7,785,299 B2  8/2010 Crawford et al.
(Continued)

FOREIGN PATENT DOCUMENTS

JP  2002333079 A  11/2002
JP  2004232671 A   8/2004
(Continued)

OTHER PUBLICATIONS

International Preliminary Report on Patentability for PCT/EP2009/007066 mailed on Apr. 21, 2011.
(Continued)

*Primary Examiner* — Tatyana Zalukaeva
*Assistant Examiner* — Benjamin Klein
(74) *Attorney, Agent, or Firm* — Kilyk & Bowersox, P.L.L.C.

(57) ABSTRACT

The invention relates to a device for reversing the blood flow for an extracorporeal blood treatment device, comprising an extracorporeal blood circuit (I), which includes an arterial blood line (108A) leading from a patient to a blood treatment unit (204) and a venous blood line (106A) leading from the blood treatment unit to the patient. Furthermore, the invention relates to an extracorporeal blood treatment device with a device for reversing the blood flow, and to a method for
(Continued)

determining the reversal of the blood flow during an extracorporeal blood treatment. The device for reversing the blood flow for an extracorporeal blood treatment device according to the invention comprises two valve bodies (102, 104) which are rotated relative to one another for reversing the blood flow. The device for reversing the blood flow according to the invention is characterized by a communication device (210) for receiving an electromagnetic high-frequency field from a read unit (270) of the extracorporeal blood treatment device and for generating at least one identifier characterizing the position of the valve bodies which can be read by the read device.

8 Claims, 5 Drawing Sheets

(51) Int. Cl.
*A61M 39/10* (2006.01)
*A61M 39/22* (2006.01)

(52) U.S. Cl.
CPC ......... *A61M 39/223* (2013.01); *F16K 11/074* (2013.01); *A61M 1/3656* (2014.02); *A61M 2039/1044* (2013.01); *A61M 2039/229* (2013.01); *A61M 2205/6018* (2013.01); *A61M 2205/6054* (2013.01)

(58) Field of Classification Search
CPC .... A61M 2039/1044; A61M 2039/229; A61M 2205/6054; F16K 11/0074
See application file for complete search history.

(56) References Cited

U.S. PATENT DOCUMENTS

| | | | |
|---|---|---|---|
| 8,784,353 B2* | 7/2014 | Maierhofer | A61M 1/367 |
| | | | 604/4.01 |
| 2004/0059315 A1 | 3/2004 | Erickson et al. | |
| 2006/0219644 A1* | 10/2006 | O'Hara, Jr. | A61M 1/3681 |
| | | | 210/782 |
| 2007/0287989 A1 | 12/2007 | Crawford et al. | |
| 2007/0293818 A1 | 12/2007 | Stout et al. | |
| 2009/0043253 A1 | 2/2009 | Podaima | |
| 2011/0040233 A1* | 2/2011 | Kassem | A61M 27/006 |
| | | | 604/9 |

FOREIGN PATENT DOCUMENTS

| | | |
|---|---|---|
| JP | 2006189130 A | 7/2006 |
| JP | 2008515547 A | 5/2008 |
| WO | 2006-042016 A2 | 4/2006 |
| WO | 2007-041843 A1 | 4/2007 |
| WO | 2007-134068 A2 | 11/2007 |

OTHER PUBLICATIONS

PCT International Search Report for PCT/EP2009/007066 mailed on Jan. 27, 2010.

* cited by examiner

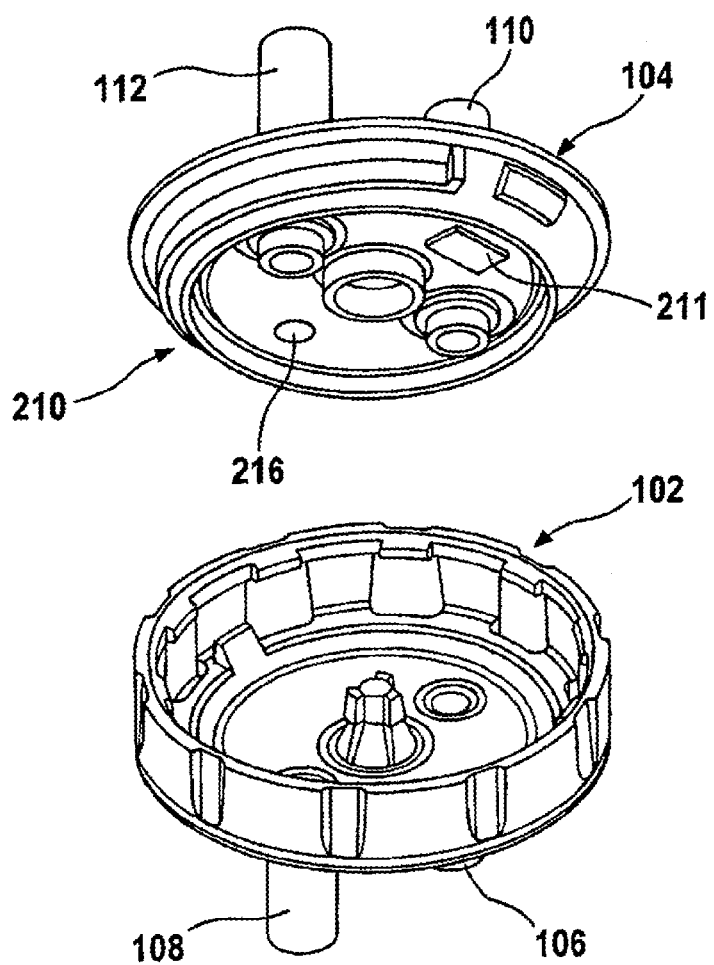

DEVICE FOR REVERSING THE BLOOD FLOW FOR AN EXTRACORPOREAL BLOOD TREATMENT DEVICE AND METHOD FOR DETERMINING THE REVERSAL OF THE BLOOD FLOW DURING AN EXTRACORPOREAL BLOOD TREATMENT

CROSS-REFERENCE TO RELATED APPLICATIONS

This application is a continuation of U.S. patent application Ser. No. 13/123,290, filed on Apr. 8, 2011, which is a national phase application based on PCT International Patent Application No. PCT/EP2009/007066, filed on Oct. 2, 2009, and German Patent Application No. 10 2008 050 848.7, filed on Oct. 8, 2008, the entire contents of which are incorporated herein by reference.

FIELD OF THE INVENTION

The present invention relates to a device for reversing blood flow, for an extra-corporeal blood treating apparatus which comprises an extra-corporeal blood circuit which has an arterial blood line outgoing from a patient which runs to a blood treating unit and a venous blood line outgoing from the blood treating unit which runs to the patient. As well as this, the present invention also relates to an extra-corporeal blood treating apparatus having a device for reversing blood flow and to a method of detecting the reversal of blood flow in extra-corporeal blood treatment.

BACKGROUND

In an extra-corporeal blood treating apparatus, such as a hemodialysis apparatus for example, the blood to be treated flows, in an extra-corporeal blood circuit, through the blood chamber of a dialyzer which is divided by a semi-permeable membrane into the blood chamber and a dialysis-fluid chamber, while in a dialysis-fluid system dialysis fluid flows through the dialysis-fluid chamber of the dialyzer. The extra-corporeal blood circuit has an arterial flexible line which runs to the blood chamber and a venous flexible line outgoing from the blood chamber. The flexible lines of the extra-corporeal blood treating apparatus are generally provided in the form of disposable items intended for once-only use. The known pieces of blood treating apparatus have a blood pump, which is usually arranged upstream of the blood chamber of the dialyzer, to ensure that there is an adequate flow of blood in the extra-corporeal blood circuit.

For highly efficient hemodialysis treatments, it is necessary for the blood to be cleansed from the patient to be fed to the extra-corporeal blood circuit at sufficiently high pumping rates. What is used for his purpose is preferably an operatively produced connection between artery and vein. Because of the bypassing of the peripheral vascular system, which presents a high resistance to flow, relatively high blow flows are obtained in the fistula or shunt, and these will be referred to in what follows as access flows. The extracorporeal blood circuit is preferably connected up by means of two needles, with blood being withdrawn through the needle directed into the artery and being returned again through the needle directed into the vein after passing through the extra-corporeal blood circuit.

For different reasons, stenoses which result in a fall in the access flow may, in the course of time, form in the fistula or shunt. If the access flow is lower than the flow in the extra-corporeal blood circuit, this causes a drop in the cleansing performance because (venous) blood which is now already cleansed mixes with uncleansed (arterial) blood. This process is referred to as access recirculation. As well as by the fall in the access flow, the process may also be encouraged to occur by unfavorable positioning of the arterial and venous needles relative to one another.

By regular measurement of the access flow, it is intended that stenoses which are formed will be detected at an early stage, to enable steps to be taken to restore the access flow at an early point in time if the flow drops below a critical level.

Measurement of the access flow is possible by, for example, duplex sonography. This, however, calls for a trained physician and a cost-intensive diagnostic unit. Also, this method cannot be used with very adipose patients. What has become established as a standard method of determining access flow is the Krivitski method (Kidney Int (July) 48: 244-250 1995). In this, with the venous and arterial needles changed over, a bolus of saline solution is injected into the extra-corporeal blood tubing system and detected in the arterial and venous blood tubing lines by means of ultrasonic sensors. This method calls for an additional cost-intensive piece of equipment and for the manual administration of saline.

From European Patent Publication EP 0 928 614 B1 is known a method of determining access flow which does not call for any other measuring devices apart from the dialysis device and which manages without the manual injection of an indicator solution. In this case, clearance is determined, with constant blood and dialysis flows, with the needles in their normal arrangement and in a reversed arrangement in succession, and the access flow is determined from the two values for clearance.

For reversing the blood flow in the extra-corporeal blood circuit, there is known from PCT Publication No. WO 2006/042016 A2 a device which prevents a loss of blood which is possible when the needles are changed over, which reduces the risk of infection and simplifies operation. Also known is operator prompting implemented on the dialysis unit to allow an access flow measurement to be made by using the known device for flow reversal.

To determine access flow, measurements of clearance are made respectively before and after the reversal of blood flow in the extra-corporeal blood circuit. The operator prompting which is implemented on the dialysis unit tell the user when the reversal of flow is to be carried out. It is a disadvantage, however, that it is not automatically detected whether the reversal of flow has in fact taken place. If, incorrectly, there has not been a reversal of flow, the measurement may give too high a value for the access flow. This may result in problems at the vascular access not being realized, especially as the user will assume that he has made a correct measurement.

There is also the risk of the blood flow not being reversed back to its original direction after a measurement has been made with the blood flow reversed. Because of the increased access circulation which occurs when flow is reversed, this will then lead to a reduced dialysis dose.

For the automatic determination of the dialysis dose by the dialyzing unit, it is necessary for the current clearance to be known at all times during the treatment. For this purpose measurements arc made at different points in time. If there is a change in the parameters which affect clearance, and in particular in the blood and dialysate flows, between the measurements, interpolation is possible on the basis of the measurements which have been made and the known treatment parameters (German Patent Publication No. DE 19928407). Because the reversal of flow affects clearance, an exact knowledge of the length of time for which flow is reversed and of the duration of the treatment with the normal direction of flow is needed for determining the dialysis dose.

There is a technique which is known by the name radio frequency identification (RFID) which is in general use for the identification and location of articles. The articles are identified with the help of electromagnetic waves. An RFID system comprises a transponder which is situated on the article and a reader for reading the identity code of the transponder. The reader generates a short-range, high-frequency electromagnetic field by which, generally, not only can data be transmitted but the transponder can also be supplied with energy.

RFID transponders are known in different forms. All RFID transponders have an aerial which is connected to a transceiver. As well as the aerial and transceiver, what are also provided are a non-erasable memory and other circuits.

Known from Japanese Patent Application Publications JP 2233079 A2, JP 24232671 A2 and JP 2002333079 A2 are valves which have an RFID transponder to enable it to be detected whether the valve is open or closed. US Patent Application Publication No. 2007/0277824 A1 describes an apparatus intended for diagnostic purposes in which correct positioning of an insert is monitored by means of an RFID transponder.

The object underlying the present invention is to provide a device for reversing blood flow for an extra-corporeal blood treating apparatus, which device, with a high degree of safety and reliability, allows the safety of the extra-corporeal blood treatment to be increased and the measurement of parameters of the blood treatment to be simplified.

As well as this, the object underlying the present invention is also to specify a method of detecting the reversal of blood flow in extra-corporeal blood treatment which is easy to operate and can be safely and reliably applied.

A further object of the present invention is to provide a blood treating apparatus which, easily and with great safety and reliability, enables a reversal of flow to be made to enable parameters of the blood treatment to be measured.

These objects are achieved in accordance with the present invention by virtue of the features of the present invention set forth herein.

SUMMARY

The device according to the present invention for reversing blood flow for an extra-corporeal blood treating apparatus has two valve-action bodies which are rotatable relative to one another. One valve-action body has a first patient-side connection for a first patient-side portion, formed by flexible tubing, of the blood line and a second patient-side connection for a second patient-side portion, formed by flexible tubing, of the blood line, while the second valve-action body has a first apparatus-side connection for a first apparatus-side portion, formed by flexible tubing, of the blood line and a second apparatus-side connection for a second apparatus-side portion, formed by flexible tubing, of the blood line.

The two valve-action bodies can be rotated relative to one another, on a common axis, between a first position which corresponds to normal blood flow and a second position which corresponds to reversed blood flow in the extra-corporeal blood circuit. In the first position, a connection for liquid is made between the first patient-side connection and the first apparatus-side connection on the one hand, and between the second patient-side connection and the second apparatus-side connection on the other hand, whereas in the second position, a connection for liquid is made between the first patient-side connection and the second apparatus-side connection on the one hand, and between the second patient-side connection and the first apparatus-side connection on the other hand.

The device according to the present invention is intended for once-only use, the flexible-tubing lines, which are likewise intended for once-only use, being able to be connected to the apparatus-side and patient-side connections.

The device according to the present invention for reversing blood flow is distinguished by having a communications arrangement for receiving a high-frequency electromagnetic field from a reading arrangement belonging to the extra-corporeal blood treating apparatus and for generating at least one code which is characteristic of the positions of the valve-action bodies and which can be read by the reading arrangement.

The communications arrangement according to the present invention of the blood treating apparatus allows the direction of flow to be identified without a connection having to be made between the blood treating apparatus and the device for reversing blood flow. The device for reversing blood flow can be operated easily because it merely needs to be introduced into the extra-corporeal blood circuit, without however having to be connected to the blood treating apparatus electrically.

In a first preferred embodiment of the present invention, provision is made for the communications arrangement to have a first RFID transponder and a second RFID transponder. The first RFID transponder transmits a first code which is characteristic of the first position of the valve-action bodies in this case, and the second RFID transponder transmits a code which is characteristic of the second position. It is thus possible for use to be made of the known RFID transponders which are also called RFID tags. These are notable for being small in size and low in cost. The existing code of the given RFID transponder allows the direction of the blood flow to be clearly identified.

A first variant of the first embodiment of the present invention relies on only one of the two RFID transponders being active. This is achieved by screening off the other RFID transponder electrically. In this embodiment, the first RFID transponder is arranged at a point characteristic of the first position, preferably on the inside face of the first or second valve-action body, while the second RFID transponder is arranged at a point characteristic of the second position, preferably on the inside face of the first or second valve-action body. The first and/or second valve-action body is screened off electrically in such a way that it is only the first RFID transponder for transmitting the code characteristic of the first position which can be read by the reading arrangement in the first position, whereas in the second position it is only the second RFID transponder for transmitting the code characteristic of the second position which can be read by the reading arrangement. It is immaterial in this case whether the transponders are then arranged on one or the other of the valve-action bodies. What is crucial is that, as a result of the valve-action bodies being turned to the two positions, one transponder is screened off electrically and the other transponder is not screened off electrically.

The electrical screening off of the transponders can be accomplished by means of suitable metallizing on the inside or outside face of the given valve. It is however also possible for the valve-action body to be made of a material which is not permeable to the high-frequency electromagnetic field.

In a particularly preferred embodiment, the first and second RFID transponders are situated opposite one another on the inside face of the first valve-action body on an axis which lies perpendicular to the axis of rotation of the valve-action bodies, the inside face of the second valve-action body being metallized to screen off the RFID transponders except for a cut-out portion which is situated opposite the first RFID transponder in the first position and opposite the second RFID transponder in the second position. Consequently, only the first RFID transponder is active in the first position while only the second RFID transponder is active in the second position. Simple but reliable identification of the direction of flow is achieved in this way.

In the particularly preferred embodiment, it is not absolutely essential for that valve-action body which is situated opposite the valve-action body which is metallized except for a cut-out portion also to be metallized to screen it off electrically. However, this valve-action body also may be metallized for better screening-off.

A second variant of the first embodiment does not make provision for the given RFID transponder to be screened off electrically but for the aerial of the given transponder to be disconnected from its transceiver. In the first position, it is only the transceiver of the first RFID transponder which is connected to an aerial whereas in the second position it is only the transceiver of the second RFID transponder which is connected to an aerial. What is achieved in this way is that the code of only one of the two RFID transponders can be read by the reading arrangement to identify the direction of flow.

The two RFID transponders may each have an aerial or may also have one common aerial. The two RFID transponders preferably have only one common aerial which can be connected to the transceiver of the given transponder or disconnected from the transceiver as a function of the position of the valve-action bodies.

The common aerial, and the transceiver of the given transponder, are connected by means of electrical connections which are formed in the valve-action body. A permanent, first electrical connection is preferably made between the aerial and the transceiver, with the second electrical connection to one of the two transceivers being made via contacts on the valve-action bodies as a function of the position of the valve-action bodies.

The RFID transponders are preferably passive transponders which obtain their energy from the high-frequency electromagnetic signal from the reading arrangement. A power supply unit is therefore not required for the device for reversing flow which is intended for once-only use. Basically, use could however also be made of active RFID transponders.

An alternative embodiment of the device according to the present invention is distinguished by the fact only a single RFID transponder is used to identify the direction of flow, which once again is preferably a passive transponder.

In this embodiment, an arrangement which detects the first and second positions of the valve-action bodies is provided which co-operates with the RFID transponder is such a way that two different codes can be read by the reading arrangement, one of which is characteristic of the first position of the valve-action bodies and of which the other code is characteristic of their other position.

The blood treating apparatus according to the present invention is distinguished by having a reading arrangement which is so designed that the code of the communications arrangement which is characteristic of the first or second position can be read.

The blood treating apparatus according to the present invention, which has an arrangement for determining a parameter of the blood treatment on the basis of a first and a second measurement of a characteristic variable made respectively before and after a reversal of blood flow, preferably has an alarm unit which co-operates with the arrangement for determining a parameter of the blood treatment in such a way that the alarm unit gives an audio and/or visual alarm if, after the first measurement and/or the second measurement, the reading arrangement has not received the codes which are respectively characteristic of the first and second positions. This ensures that the blood flow has in fact been reversed for the measurement to be made and/or that the normal blood flow has been established again after the measurement. It is immaterial in this case which are the parameters of the blood treatment which are to be determined. The only thing that is crucial is that the measurement calls for a reversal of blood flow. Clearance, for example, may be measured.

In practice, the problem arises that a plurality of pieces of blood treating apparatus are operated in positions closely adjacent to one another at a treatment center, which means that it has to be ensured that there is a clear correlation between the reading arrangement of the piece of blood treating apparatus and the associated device for reversing flow. A preferred embodiment of the blood treating apparatus according to the present invention therefore has an arrangement for recognizing the communications arrangement of the associated device for reversing blood flow. The arrangement for recognizing the communications arrangement has means which are so designed that a change between the codes characteristics of the first and second positions within a preset interval of time can be detected. Thus, by turning the valve-action bodies of that device for reversing flow which is associated with the blood treating apparatus, the user is able to produce an identification signal which is recognized by the associated blood treating apparatus.

The device according to the present invention may be used not only for reversing the flow of blood in an extra-corporeal blood circuit of an extra-corporeal blood treating apparatus but also for reversing flow in other systems handling liquids. One example of a use of the device according to the present invention other than in an extra-corporeal blood circuit is the reversal of flow to flush clean a filter in a system handling liquids.

Various embodiments of the present invention will be explained in detail in what follows by reference to the drawings.

BRIEF DESCRIPTION OF THE DRAWINGS

FIG. 6A is a perspective view of the first valve-action body of a further embodiment of a device according to the present invention for reversing flow, FIG. 6B is a perspective view of the second valve-action body of the further embodiment of a device according to the present invention for reversing flow.

DETAILED DESCRIPTION

Figure 1:
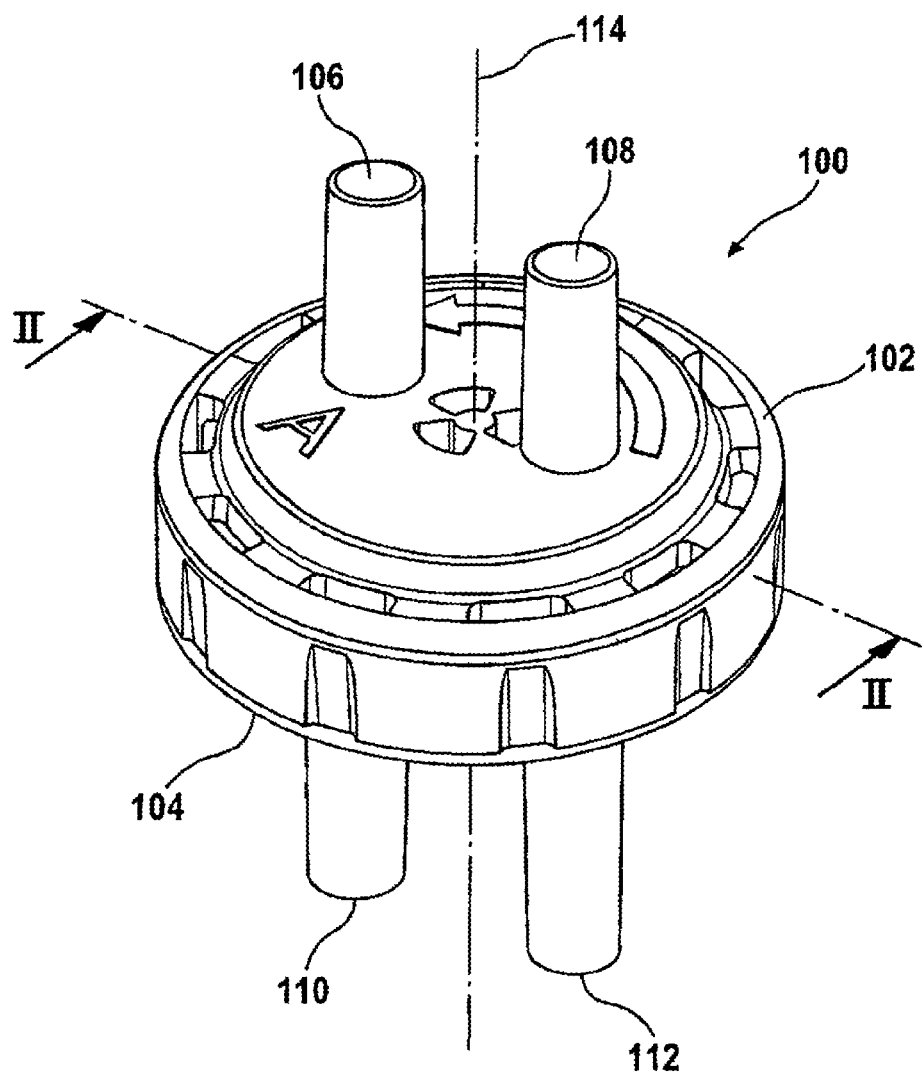
FIG. 1 is a perspective view showing an embodiment of device according to the present invention for reversing blood flow in the extra-corporeal blood circuit.
Figure 2:
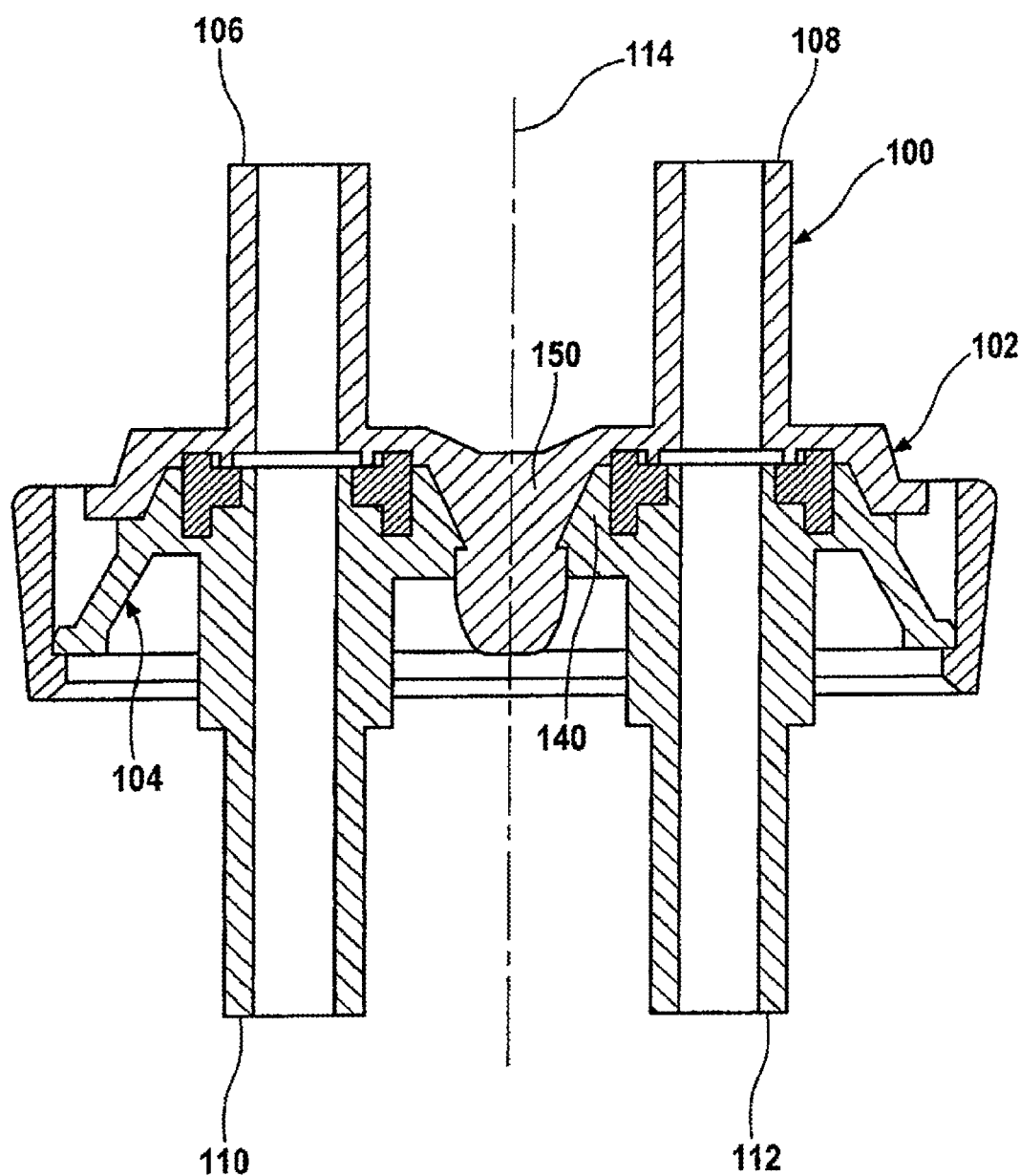
FIG. 2 is a section through the device shown in FIG. 1 taken on line II-II.

FIG. 1 is a perspective view showing the device according to the present invention for reversing flow which is intended for once-only use. The device 100 for reversing flow comprises a first valve-action body 104 which is at the bottom in FIG. 1 and a second valve-action body 102 which is at the top in FIG. 1. FIG. 2 is a view in section of the device 100 for reversing flow.

In itself, the device 100 for reversing flow is part of the prior art. The device according to the present invention for reversing flow differs from the known device in that the device according to the present invention has a communications arrangement which will be described in detail below. FIGS. 1 and 2 show the known device for reversing flow, with the communications arrangement not being shown.

Figure 3A:
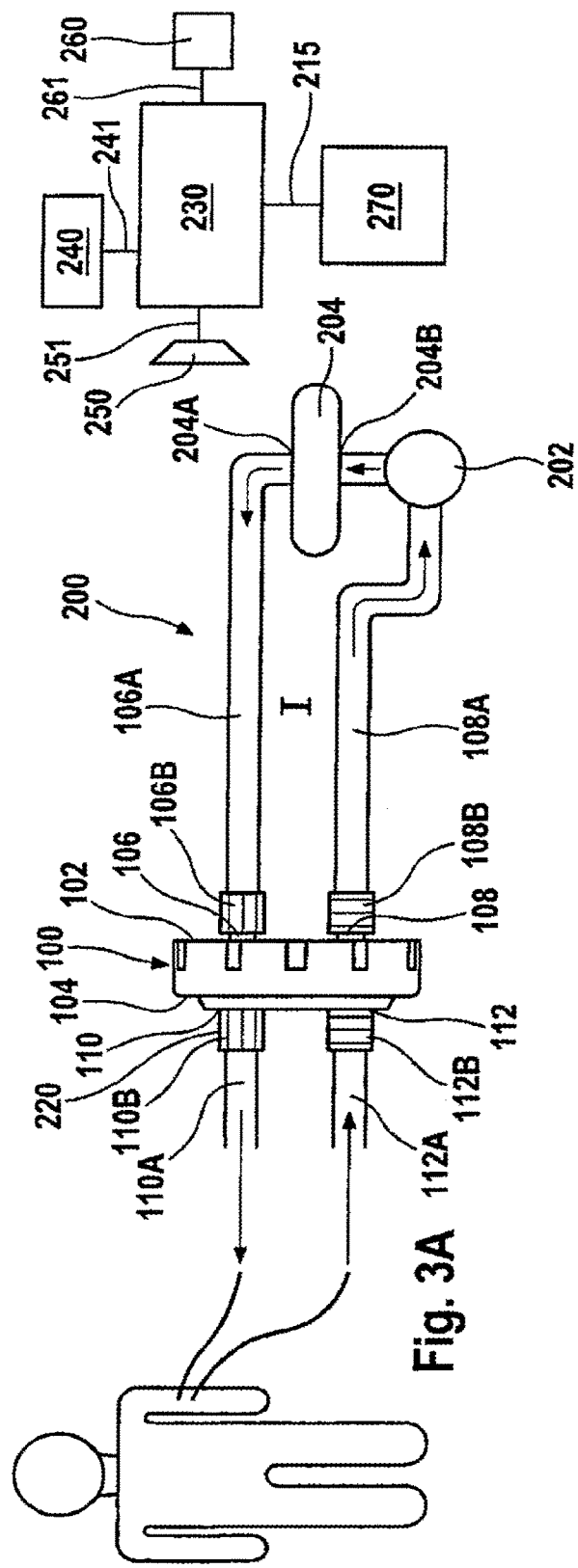
FIG. 3A is a highly simplified schematic view of the extra-corporeal blood treating apparatus according to the present invention which has the device for reversing blood flow, with the blood flow not reversed.
Figure 3B:
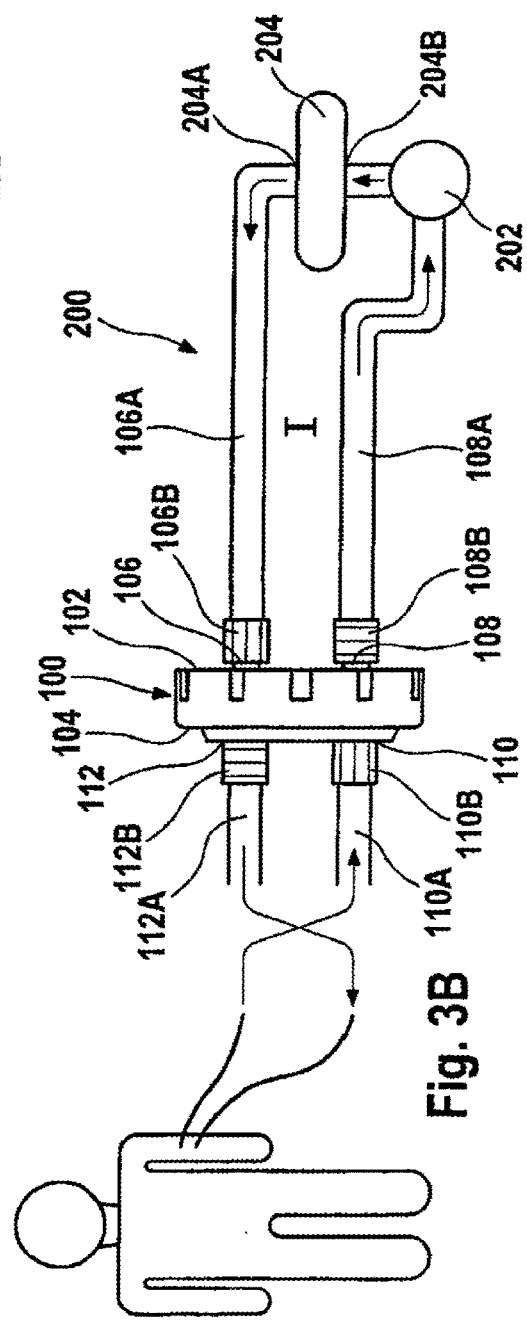
FIG. 3B shows the extra-corporeal blood treating apparatus shown in FIG. 3A, with the blood flow reversed.

The construction and operation of the known device for reversing flow (FIGS. 1 and 2) are described in detail in PCT Publication No. WO 2006/042016 A2, the disclosure of which is hereby explicitly incorporated by reference in its entirety. Because the device for reversing flow has already been described in detail in PCT Publication No. WO 2006/042016 A2, it will only be the components which are material to the present invention which will be explained below. The device for reversing flow is connected into the extra-corporeal blood circuit I of the blood treating apparatus 200. FIGS. 3A and 3B show the device 100 for reversing flow when connected into the extra-corporeal blood circuit I.

The first valve-action body 104 of the device for reversing flow has a first patient-side connection 110 and a second patient-side connection 112, the first patient-side connection 110 having connected to it a first portion 110A, which is formed by flexible tubing, of the blood line 110A, 112A, which first portion 110A is connected to the patient, and the second patient-side connection 112 having connected to it a second portion 112A, which is formed by flexible tubing, of the blood line 110A, 112A, which second portion 112A is connected to the patient. The second valve-action body 102 has a first apparatus-side connection 106 and a second apparatus-side connection 108, the first apparatus-side connection 106 having connected to it a first portion 106A, formed by flexible tubing, of the blood line, which first portion 106A is connected to the outlet 204A of the blood treating unit 204, and in particular of the dialyzer, of the extra-corporeal blood treating apparatus 200, and the second apparatus-side connection 108 having connected to it a second portion 108A, which is formed by flexible tubing, of the blood line, which second portion 108A is connected to the inlet 204B of the blood treating unit 204. As well as the blood treating unit 204, the blood treating apparatus 200 also has a pump 202 which is connected into that portion 108A, formed by flexible tubing, of the blood line which runs to the inlet 204B of the blood treating unit 204. FIG. 3A shows the extra-corporeal blood circuit I of the blood treating apparatus 200 when the blood flow is not reversed, whereas FIG. 3B shows the blood treating apparatus having the device for reversing flow when the blood flow is reversed.

The second valve-action body 102 is in the form of a cap-like body, whereas the first valve-action body 104 is in the form of an inserted part. The first valve-action body 104 is seated in the second valve-action body 102, with the two valve-action bodies 102, 104 being able to be rotated relative to one another between a first position and a second position on a central axis 114. Provided at the ends of the portions of the blood line which are formed by flexible tubing are matching connecting members 106B, 108B, 110B, 112B by which the portions of flexible tubing can easily be connected to the matched, corresponding connecting members 106, 108, 110, 112 on the device 100 for reversing flow, and detached again therefrom.

FIG. 3A shows the first position, in which a connection for liquid is made between the first apparatus-side connection 106 and the first patient-side connection 110, and a connection for liquid is made between the second apparatus-side connection 108 and the second patient-side connection 112. When the first valve-action body 104 is turned through 180° relative to the second valve-action body 102 (FIG. 3B), a connection for liquid is made between the first apparatus-side connection 106 and the second patient-side connection 112 and a connection for liquid is made between the second apparatus-side connection 108 and the first patient-side connection 110, which means that the direction of flow in the extra-corporeal blood circuit I is reversed.

For the user, it is thus possible to preset the direction of flow in the blood circuit by turning the two valve-action bodies 102, 104. The device 100 for reversing flow preferably makes provision for the two valves bodies 102, 104 to be locked by latching in the first and second positions.

Figure 4A:
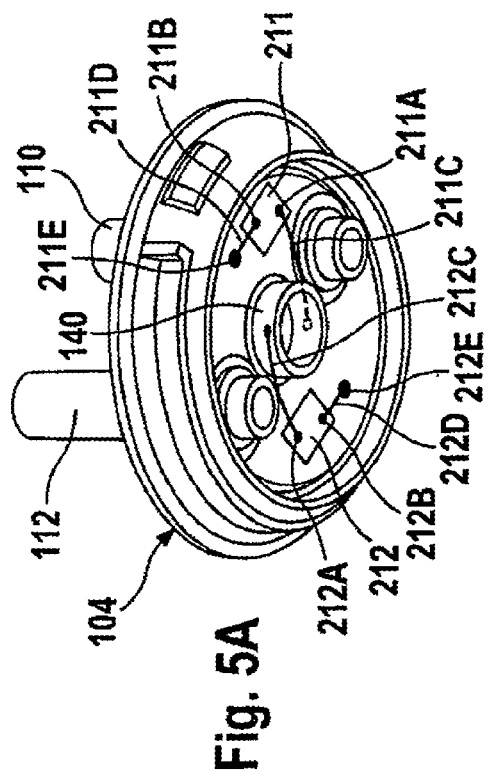
FIG. 4A is a perspective view of the first valve-action body of a first embodiment of the device according to the present invention for reversing flow.
Figure 4B:
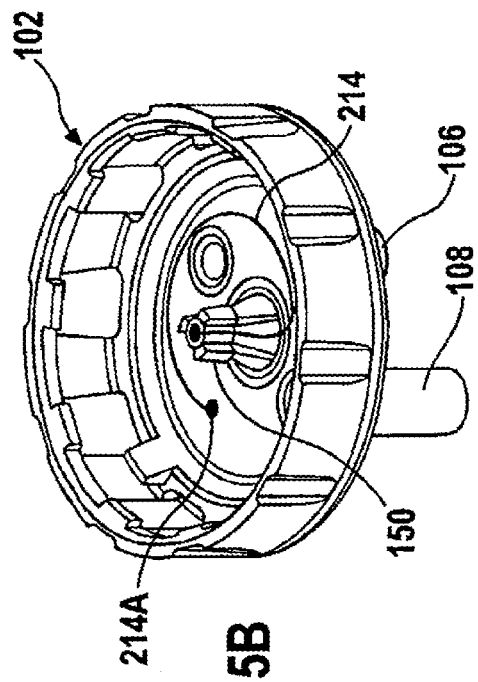
FIG. 4B is a perspective view of the second valve-action body of the first embodiment of the device according to the present invention for reversing flow.

FIGS. 4A and 4B are exploded views showing a first embodiment of device 100 according to the present invention for reversing flow which has a communications arrangement 210 which communicates with the reading arrangement 270 of the blood treating apparatus 200. The reading arrangement 270, which is connected to the central control unit of the dialysis apparatus by a data line 215, generates a high-frequency electromagnetic field in the region close to the blood treating apparatus 200 and the communications arrangement 210 of the device 100 for reversing flow receives this field. The communications arrangement 210 and the reading arrangement 270 together form an RFID system for identifying the direction of flow in the extra-corporeal blood circuit I.

The communications arrangement 210 has a first RFID transponder 211 and a second RFID transponder 212, which are only shown in schematic form in the drawings. The two transponders 211, 212 have an aerial (not shown) and a transceiver (not shown) and a non-erasable memory and other circuits. Because the construction and operation of an RFID transponder are known to the person skilled in the art, there is no need for any detailed description.

The two RFID transponders 211, 212, which are of a very small overall size, are arranged opposite one another on the inside face of the first valve-action body 104. They lie on an axis which extends perpendicularly to the axis 114 on which the two valve-action bodies 102, 104 can be turned. The axis on which the transponders lie extends perpendicularly to the axis which extends through the two apparatus-side connections 106, 108. The transponders 211, 212 are thus arranged in positions offset at 90° from these connections 106, 108.

The RFID transponders 211, 212 which are arranged in the first valve-action body 104 are screened off electrically by the second valve-action body 102 provided the two valve-action bodies 102, 104 are not in one of their two positions. For the electrical screening-off, the second valve-action body 102 is metallized on the inside face facing towards the first valve-action body 104. However, the metallizing for electrical screening-off does not extend over the whole of the inside face. Instead, a sector 213 in the form of a sector of a circle is left free of metallizing. This sector in the form of a sector of a circle is arranged in a position offset at 90° from the apparatus-side connections 106, 108 of the second valve-action body 102 and lies on the circular path along which the two transponders 211, 212 on the second valve-action body 104 move when the two valve-action bodies 102, 104 are turned relative to one another.

The transponders 211, 212 and the region 213 free of metallizing are so arranged that the un-screened-off region 213 is situated opposite the first transponder 211 in the first position, which means the first transponder 211 is then active but the second transponder 212 is screened off electrically. In the second position on the other hand, the second transponder 212 is active whereas the first transponder 211 is screened off electrically.

For screening-off, metallizing may also be provided on the outside face or on both faces. Rather than being metallized on its surface, the valve-action body may also itself be composed of a material which is not permeable to the high-frequency electromagnetic field from the reading arrangement. For better electrical screening-off, the second valve-action body also is preferably metallized on the inside face. This metallizing may however preferably extend over the whole of the inside face of the second valve-action body.

The two transponders are preferably passive transponders which obtain their energy from the high-frequency electrical field from the reading arrangement 270. When the two valve-action bodies are in the first position, the reading arrangement 270 reads from the first RFID transponder 211 a code characteristic of the first position, whereas the reading arrangement 270 reads a code characteristic of the second position from the second transponder 212 when the two valve-action bodies are in the second position. The first code is, for example, a code which is made up of a serial number belonging to the RFID transponder and an identifier "1", whereas the second code is a code which is made up of the serial number of the second transponder and an identifier "2". The two transponders preferably have a common serial number so that the transponders 211, 212 can be distinguished from transponders belonging to other devices for reversing flow which may likewise be situated in the near field of the reading arrangement.

The reading of the code characteristic of the direction of flow in the extra-corporeal blood circuit can be performed continuously or at given intervals during the blood treatment by the reading arrangement.

Figure 5A:
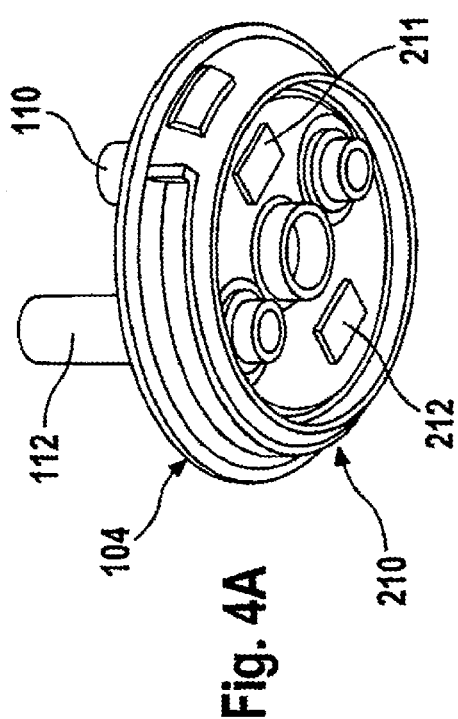
FIG. 5A is a perspective view of the first valve-action body of a second embodiment of a device according to the present invention for reversing flow.
Figure 5B:
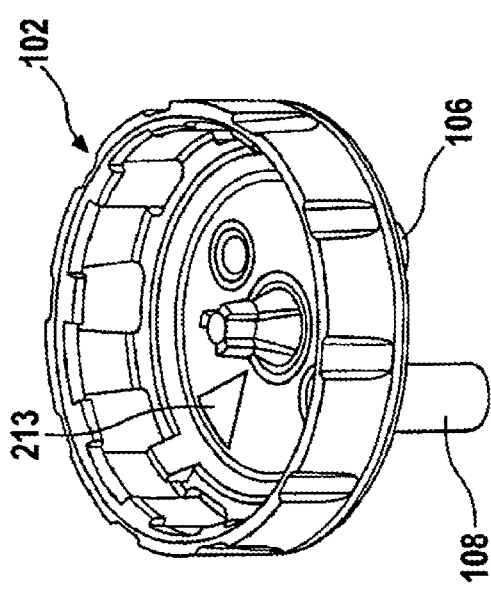
FIG. 5B is a perspective view of the second valve-action body of the second embodiment of the device according to the present invention for reversing flow.

FIGS. 5A and 5B show a second embodiment of a device according to the present invention for reversing flow which differs from the first embodiment in that the activation or de-activation, as the case may be, of the two RFID transponders is accomplished not by electrical screening-off but by connecting the transceiver of only one of the two transponders to a common aerial. Parts which correspond to one another have therefore been given the same reference numerals. The two RFID transponders 211, 212 do not have internal aerials which are part of the RFID tags as they do in the case of the first embodiment but have one common aerial 214 which at any given time is placed in connection with the transceiver (not shown) of one or other of the transponders 211, 212. The external aerial 214 is a spiral printed-circuit-type conductor which is arranged on the inside face of the second valve-action body 102 which faces towards the first valve-action body 104. In this embodiment, the valve-action bodies 102, 104 do not screen off the transponders 211, 212 electrically.

The two RFID transponders 211, 212 have respective pairs of connections 211A, 211B and 212A, 212B for the aerial. The respective first connections 211A, 212A of the two transponders 211, 212 are connected via respective connecting lines 211C, 212C to a central hollow cylindrical boss 140 on the first valve-action body 104 which, when the two valve-action bodies 102, 104 are plugged together (FIG. 2), surrounds a central projecting boss 150 on the second valve-action body 102. The cylindrical boss 140 on the first valve-action body 104 and the projecting boss 150 on the second valve-action body 102 are each metallized so that an electrical connection is made between the two valve-action bodies.

The respective second connections 211B, 212B of the two transponders 211, 212 are connected to respective electrical contacts 211E, 212E by respective electrical connecting lines 211D, 212D. The two electrical contacts 211E and 212E are arranged opposite one another on the inside face of the first valve-action body 104 which faces towards the second valve-action body 102. They lie on an axis which extends perpendicularly to the axis of rotation 114. The axis on which the two contact-making points lie extends at right angles to the axis on which the patient-side connections 110, 112 on the first valve-action body 104 lie, i.e. the contacts are arranged to be offset at 90° from these connections.

The first connection of the common aerial 214 is electrically connected to the projecting boss 150 on the second valve-action body 102, which means that there is a permanent electrical connection made to the two first connections 211A, 212A of the two transponders 211, 212. The second connection of the aerial 214 is electrically connected to a sliding contact 214A which is arranged on the inside face of the second valve-action body 102 which faces towards the first valve-action body 104.

When the two valve-action bodies 102, 104 are in the first position, the sliding contact 214A on the second valve-action body 102 makes contact with the first contact 211E on the first valve-action body 104, whereas in the second position the sliding contact 214A makes contact with the second contact 212E on the second valve-action body 104. Consequently, in the first position it is only the transceiver of the first transponder 211, which transceiver is not in fact shown, which is connected electrically to the aerial 214, whereas in the second position it is only the second transceiver of the second transponder 212, which second transceiver is not explicitly shown, which is connected electrically to the aerial 214.

As in the first embodiment, the reading arrangement 270 is only able to read the code of the first transponder 211 in the first position and in the second position is only able to read the code of the second transponder 212. It is possible in this way for the direction of flow to be clearly identified.

FIGS. 6A and 6B are simplified schematic views showing a further embodiment of a device according to the present invention for reversing flow which differs from the other two embodiments in that the communications arrangement has only a single RFID transponder. Parts which correspond to one another are once again given the same reference numerals.

In the alternative embodiment shown in FIGS. 6A and 6B, the communications arrangement 210 has an arrangement 216, which is only shown schematically, which detects the first and second positions of the valve-action bodies 102, 104. An arrangement of this kind for detecting the positions of the valve-action bodies 102, 104, may for example be a position-dependent switch or resistive or capacitive angle sensors. The only crucial fact is that the arrangement 216 for detecting position for the single RFID transponder 211 generates a signal which is characteristic of the first or second position. In this embodiment, the single RFID transponder has two codes for the two positions of the valve-action bodies, which codes are read by the reading arrangement 270.

The extra-corporeal blood treating apparatus may be a conventional blood treating apparatus, such as a dialysis apparatus for example, which, as well as the known components, also has the reading arrangement 270 according to the present invention. The automatic identification of the direction of flow in the extra-corporeal blood circuit I is of advantage particularly when the blood treating apparatus has an arrangement 240 for determining a parameter of the blood treatment, such as clearance for example, in a way which calls for a measurement of a characteristic variable of the blood before and after reversal of the blood flow. Arrangements of this kind for determining parameters of the blood treatment are part of the prior art.

The arrangement 240 for determining a parameter of the blood treatment is only schematically indicated in FIGS. 3A and 3B. The arrangement 240 for determining the parameter of the blood treatment is connected to the central control unit 230 of the blood treating apparatus by a data line 241. As well as controlling the individual sub-assemblies of the blood treating apparatus, the central control unit 230 is also responsible for controlling the reading arrangement 270 and the measuring arrangement 240.

As well as this, the blood treating apparatus 200 also has an alarm unit 250, which is connected to the control unit 230 by a data line 251, and a display unit 260, which is likewise connected to the control unit, by a data line 261.

For the making of a measurement of a characteristic variable before and after the reversal of blood flow for the purpose of determining a parameter of the blood treatment, the operator prompting by the blood treating apparatus makes provision for the user to be requested to reverse the blood flow in the extra-corporeal blood circuit by turning the two valve-action bodies 102, 104 of the device 100 manually. This request is signalled to the user by the display unit 260.

The first measurement having been made with normal blood flow, the reading arrangement 270 checks to see whether the user who is requested to reverse the blood flow has reversed the blood flow by turning the valve-action bodies 102, 104. If the user has not obeyed this request, the reading arrangement 270 finds this to be the case because it is not the code for the second position of the valve-action bodies which is read but the code for the first position. The reading arrangement 270 then generates a signal for an alarm, which the alarm unit 250 receives via the control unit 230. The alarm unit 250 then gives an audio and/or visual alarm as a renewed request to the user to reverse the blood flow.

The second measurement having been made with the blood flow reversed, the user is again requested, on the display unit 260, to reverse the blood flow. The reading arrangement 270 then makes another check, to see whether the blood flow is taking place in the original direction. If it is not, an alarm is again given. The reading arrangement finds that the position is correct from the fact that it is not the code for the second position of the valve-action bodies 102, 104 which is read but the code for their first position.

The routine for performing the measurement is preferably interrupted if the reading arrangement 270 has not read the correct direction of flow. Not only does this prevent incorrect measurements, but it also ensures that the extra-corporeal blood treatment is not conducted with a reversed blood flow after the measurements. With the reading arrangement 270, it is not only possible for the direction of flow to be detected but also for it to be found whether the valve-action bodies 102, 104 are in the correct latched position in which a connection for liquid is made between the connections. With the device for reversing flow which is known from PCT Publication No. WO 2006/042016 A2, there could, for example, be a risk that the valve-action bodies have not latched into one of the two positions but have been misrotated relative to this latched position. If this were the case, both the transponders 211, 212 would be inactive, which the reading arrangement 270 would detect because the appropriate code would not be read. This would also be the case when, although a connection for liquid had been made, the lumens of the connections situated opposite one another were not exactly in line with one another, which would mean that only a narrow gap was left for the blood to flow through. Because this might result in damage being caused to the blood by hemolysis, the blood treating apparatus 200 according to the present invention preferably makes provision for the blood flow to be interrupted if the reading arrangement 270 fails to detect a proper alignment of the valve-action bodies 102, 104 relative to one another in the two positions. The reliability and safety of the blood treatment and of the measurements are further increased by this mechanism.

In practice, there also arises the problem that a plurality of pieces of blood treating apparatus are operated closely adjacent to one another. There is therefore a requirement for that the device for reversing blood flow which is associated with the given piece of blood treating apparatus to be identified.

In the blood treating apparatus 200 according to the present invention, automatic identification is performed by a test of the operation of the device 100 for reversing blood flow. One or more devices for reversing blood flow having been detected, the user is requested by the blood treating apparatus 200, on the display unit 260, to turn, relative to one another, the valve-action bodies 102, 104 of that device 100 for reversing blow which is associated with the given piece of blood treating apparatus. By this means, the two RFID transponders 211, 212 are activated in succession within a preset interval of time which the user requires to turn the valve-action bodies 102, 104. The reading arrangement 270 of the blood treating apparatus then detects the associated device for reversing flow by virtue of the fact that a change between the codes characteristic of the two positions takes place within a preset interval of time. The reading arrangement has appropriate means for this. The common serial numbers in the two codes for the direction of flow which are read by the reading arrangement then allow the associated device for reversing flow to be identified.

The menu-based prompting by the dialysis apparatus may also make provision for the measurements for determining a parameter of the blood treatment to be performed automatically solely as a result of the associated device being detected without any further input by the user being required.

Together with the device for reversing flow, the blood treating apparatus according to the present invention also has other advantages and these are explained below.

As well as native fistulas and PTFE grafts, what are used precisely when vascular conditions are difficult are twin-lumen central venous catheters. In these, arterial and venous flexible blood tubes are connected to two different parts of the catheter. To prevent recirculation, the two ends of the catheter which are fixed in place in the vestibule are separated from one another in space (by about 2 cm). In a fully functional catheter, the withdrawal (arterial) of blood takes place through the shorter of the two ends and the return (venous) takes place through the longer end. It may occasionally happen that the desired blood flow is not obtained in this configuration, the reasons for this not having been fully clarified (see Depner, "Catheter Performance", Seminars in Dialysis 14/6 (2001), pages 425-431). In such cases, the connections are typically changed over at the catheter by the nursing staff, as a result of which the desired flow is often obtained again. In the literature, there are indications that a treatment in which the direction of flow is changed over takes place in up to 30% of cases (N. Pannu et al., "Optimizing dialysis delivery in tunneled dialysis catheters", ASAIO Journal 52/2 (2006), pages 57-162). The changeover results however in increased access recirculation, which causes a reduction in the efficiency of the dialysis.

By the use of the device according to the present invention for reversing flow in the system of flexible blood tubing, it is now possible on the other hand for the changeover to be performed easily and with little risk of infection. On the other hand, automatic recording of the orientation of the flexible access tubes for blood in the dialysis unit is possible as a result of the automatic detection of position by means of the RFID reader in the dialysis unit. A record of treatments in which there are access problems can be kept automatically in this way. If, in addition, too low a clearance is detected when a measurement of clearance is made, the interchange of the connections of the catheter may, at the same time, be detected as a reason for the measurement of the excessively low clearance and can thus be distinguished from other possible reasons, e.g. clotting of the dialyzer.

The embodiments of the present invention which are shown in the drawings are merely embodiments which are intended to show a particularly preferred use of the present invention in the mechanical changeover valve which is known from PCT Publication No. WO 2006/042016 A2. The mechanical changeover valve as such may however be of a design different from that described in PCT Publication No. WO 2006/042016 A2.

The invention claimed is:

1. A device for reversing blood flow, for an extra-corporeal blood treating apparatus which comprises an extra-corporeal blood circuit which has an arterial blood line outgoing from a patient which runs to a blood treating unit and a venous blood line outgoing from the blood treating unit which runs to the patient, the device for reversing flow comprising:
a first valve-action body having a first patient-side connection for a first patient-side portion, formed of flexible tubing, of the blood line and a second patient-side connection for a second patient-side portion, formed of flexible tubing, of the blood line;
a second valve-action body having a first apparatus-side connection for a first apparatus-side portion, formed of flexible tubing, of the blood line and a second apparatus-side connection for a second apparatus-side portion, formed of flexible tubing, of the blood line, the first and second valve-action bodies being rotatable with respect to each other on an axis in such a way that,
in a first relative position between the first and second valve-action bodies, a connection for liquid is made between the first patient-side connection and the first apparatus-side connection, and a connection for liquid is made between the second patient-side connection and the second apparatus-side connection, and
in a second relative position between the first and second valve bodies, connection for liquid is made between the first patient-side connection and the second apparatus-side connection, and a connection for liquid is made between the second patient-side connection and the first apparatus-side connection;
a communications arrangement configured to receive a high-frequency electromagnetic field from a reading arrangement belonging to the extra-corporeal blood treating apparatus and to generate at least one code which is characteristic of one of the first and second relative positions of the valve-action bodies and which is readable by the reading arrangement,
wherein the communications arrangement includes an RFID transponder configured to identify a direction of blood flow and to transmit a code characteristic of the first relative position and a code characteristic of the second relative position; and
a detection arrangement configured to detect the first and second relative positions of the valve-action bodies and to co-operate with the RFID transponder in such a way that, in the first relative position, the code characteristic of the first relative position is readable by the reading arrangement and, in the second relative position, the code characteristic of the second position is readable by the reading arrangement.

2. The device according to claim 1, wherein the RFID transponder is a passive transponder.

3. A blood treating apparatus, comprising:
the device for reversing blood flow according to claim 1;
an arterial blood line;
a venous blood line;
a blood treating unit; and
an RFID reader;
wherein the apparatus is configured to carry out an extra-corporeal blood treatment in which, in the extra-corporeal blood circuit, the blood of a patient flows via the arterial blood line to the blood treating unit and via the venous blood line from the blood treating unit to the patient, the device for reversing blood flow being connected into the arterial and venous blood lines, the RFID reader being configured such that the code characteristic of the first or second relative position is readable from the communications arrangement of the device for reversing blood flow; and
wherein the apparatus further comprises:
an arrangement configured to determine a parameter of the blood treatment on the basis of a first measurement of a characteristic variable before the reversal of blood flow and a second measurement of a characteristic variable after the reversal of blood flow; and
an alarm unit configured to co-operate with the arrangement configured to determine a parameter of the blood treatment in such a way that the alarm unit provides an alarm if, after the first measurement, the RFID reader has not received the code characteristic of the first relative position and if, after the second measurement, the RFID reader has not received the code characteristic of the second relative position.

4. A method of treating blood, comprising:

connecting the device for reversing blood flow according to claim 1 to an extra-corporeal blood circuit, the extra-corporeal blood circuit comprising an arterial blood line, a venous blood line, and a blood treating unit;

connecting the arterial blood line and the venous blood line to a patient;

carrying out an extra-corporeal blood treatment in which, in the extra-corporeal blood circuit, the blood of a patient flows via the arterial blood line to the blood treating unit and via the venous blood line from the blood treating unit to the patient, the device for reversing blood flow being connected into the arterial and venous blood lines;

turning the valve-action bodies to produce an identification signal; and recognizing the communications arrangement of the device for reversing blood flow to detect a change between the code characteristics of the first and second relative positions within a preset interval of time.

5. The device according to claim 1, wherein the detection arrangement comprises a position-dependent switch.

6. The device according to claim 1, wherein the detection arrangement comprises a resistive angle sensor.

7. The device according to claim 1, wherein the detection arrangement comprises a capacitive angle sensor.

8. A system comprising an extra-corporeal blood treating apparatus and the device of claim 1, wherein the extra-corporeal blood treating apparatus comprises an RFID reader configured to produce a high-frequency electromagnetic field and configured to read at least one code that is characteristic of one of the first and second positions of the valve-action bodies.

* * * * *